United States Patent [19]

Lopes et al.

[11] Patent Number: 4,715,980
[45] Date of Patent: Dec. 29, 1987

[54] ANTIMICROBIAL SANITIZING COMPOSITION CONTAINING N-ALKYL AND N-ALKENYL SUCCINIC ACID AND METHODS FOR USE

[75] Inventors: John A. Lopes; James H. Stanton, both of Grosse Ile, Mich.

[73] Assignee: Diversey Wyandotte Corporation, Wyandotte, Mich.

[21] Appl. No.: 840,336

[22] Filed: Mar. 17, 1986

[51] Int. Cl.$^4$ .............................................. C11D 3/48
[52] U.S. Cl. .................................. 252/106; 252/174.19; 252/114.21; 252/554; 252/558; 252/DIG. 14; 252/542; 252/142; 422/28; 514/557; 514/558
[58] Field of Search ............. 252/106, 174.19, 174.21, 252/DIG. 14, 550, 531, 554, 142, 542, 135, 558; 422/28; 514/557, 558, 560

[56] References Cited

U.S. PATENT DOCUMENTS

| | | | |
|---|---|---|---|
| 2,381,852 | 8/1945 | Hochwalt | 117/138.5 |
| 2,692,204 | 10/1954 | Nowak | 106/15 |
| 2,878,190 | 3/1959 | Dvorkovitz | 252/152 |
| 3,150,096 | 9/1964 | Schmidt | 252/106 |
| 3,438,906 | 4/1969 | Duvall | 252/106 |
| 3,525,696 | 8/1970 | Schmidt | 252/106 |
| 3,661,787 | 5/1972 | Brown | 252/109 |
| 3,990,983 | 11/1976 | Lamberti | 252/174.19 |
| 4,021,376 | 5/1977 | Lamberti et al. | 252/558 |
| 4,032,465 | 6/1977 | Bauer et al. | 252/135 |
| 4,167,561 | 9/1979 | Lamberti et al. | 252/174.19 |
| 4,177,294 | 12/1979 | Lehmann et al. | 252/106 |
| 4,277,378 | 7/1981 | Tsujii et al. | 252/546 |
| 4,382,871 | 5/1983 | Lamberti et al. | 252/174.19 |
| 4,404,040 | 9/1983 | Wang | 252/106 |
| 4,581,161 | 4/1986 | Nedonchelle | 252/174.19 |

FOREIGN PATENT DOCUMENTS

| | | |
|---|---|---|
| 553057 | 2/1953 | Canada . |
| 657564 | 2/1963 | Canada . |
| 2310246 | 9/1974 | Fed. Rep. of Germany . |

*Primary Examiner*—Josephine L. Barr
*Attorney, Agent, or Firm*—Arnold S. Weintraub

[57] ABSTRACT

An antimicrobial sanitizing composition concentrate suitable for use in food preparation and handling equipment and capable of being diluted with a major amount of diluent and the resulting aqueous use solution. The concentrate containing:

(a) a dicarboxylic acid having the general formula:

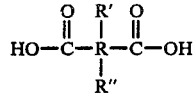

wherein R is a saturated or unsaturated hydrocarbon moiety having two carbon atoms; R' is a substituted or unsubstituted n-alkyl or n-alkenyl moeity having between about 6 and about 12 carbon atoms, and R" is a functional group selected from the group consisting of hydrogen, alcohols, amines and sulfates;

(b) a solubilizer;

(c) an acid capable of yielding a pH below about 5.0 upon dilution of the concentrate to a use solution; and (d) a diluent.

26 Claims, No Drawings

ANTIMICROBIAL SANITIZING COMPOSITION CONTAINING N-ALKYL AND N-ALKENYL SUCCINIC ACID AND METHODS FOR USE

BACKGROUND OF THE INVENTION

1. Field of the Invention

This invention relates to cleaning and sanitizing compositions which contain n-alkyl and/or n-alkenyl succinic acids as the active antimicrobial agent.

2. Background of the Prior Art

Various chemicals exhibit varying degrees of antimicrobial activity. Among these are short-chain monocarboxylic acids having less than twenty carbon atoms, quaternary ammonium compounds and hexachlorophene compounds. These compounds have been admixed with various surfactants and water to yield aqueous sanitizing solutions.

It has been found that the antimicrobial activity of these compounds can be incresed when the sanitizer solution is acidified to a pH below about 5. Acid sanitizing solutions of this type are generally employed in food, beverage, brewery and other industries as a clean-in-place, sanitizing solution for processing equipment.

Generally, antimicrobial solutions containing these antimicrobial agents are undesirable for use in food equipment cleaning applications. Residual amounts of the acid sanitizing solutions which remain in the equipment after cleaning can impart unpleasant tastes and odors to food. The cleaning solutions are difficult to rinse from the cleaned surfaces. Larger amounts of water are required to effectively completely remove conventional sanitizing solutions. Those sanitizers containing halogens can be corrosive to metal surfaces of food plants. Quaternary ammonium compounds strongly adhere to sanitized surfaces even after copious rinsing and may interfere with desired microbial growth during food processing; e.g. fermentation.

It has, also, been found that the antimicrobial activity of conventional acid sanitizing solutions can be adversely affected by the hardness of the water used in and with the solution. A marked decrease in antimicrobial activity has been noted at water hardness above about 500 ppm. Therefore, in order to assure sufficient antimicrobial activity, the hardness of water must be carefully adjusted to maintain the harness below about 500 ppm.

The acid sanitizing solutions presently available are effective against gram negative and gram positive bacteria such as *E. coli* and *Staph. aureaus* but are not as efficacious on any yest contamination which can be present. In many applications control of yeast infestations requires a separate solution than that which is used to eliminate gram negative and gram positive bacteria. Use of two solutions can be costly and time consuming.

Thus, it is desirable to provide an antimicrobial solution which is equally effective on gram negative and gram positive bacteria and on yeast. It is also desirable that the antimicrobial activity of the solution be unaffected by water hardness.

SUMMARY OF THE INVENTION

In accordance herewith, there is provided an antimicrobial sanitizing composition concentrate which is capable of being diluted with a major amount of a food grade diluent to form an antimicrobial use solution. The concentrate composition hereof, generally, comprises:

(a) a dicarboxylic acid having the general formula:

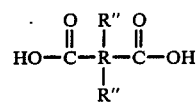

wherein R is a saturated or unsaturated hydrocarbon moiety having two carbon atoms; R' is a substituted or unsubstituted n-alkyl or n-alkenyl moiety having between about 6 and about 12 carbon atoms; and R" is a functional group selected from the group consisting of hydrogen, and alcohols; where R' is substituted, suitable substituents include thiols, methane thiols, amines, methoxy compounds and various aromatic compounds which aid in solubilization of the dicarboxylic acid.

(b) a solubilizer;

(c) an anionic diluent; and (d) an acid capable of yielding a solution pH less than or equal to about 5.0 upon dilution of the concentrate to a use solution; and The present invention, also, provides an antimicrobial "use solution" which is particularly suited for "in place" cleaning. The use solution comprises:

(a) between about 10 parts per million (ppm) to about 500 ppm of the defined dicarboxylic acid;

(b) at least about 10 pm of the solubilizer;

(c) the acid sufficient to yield a pH less than or equalto 5; and (d) a suitable anionic diluent.

The present invention further contemplates a method of using the composition in cleaning "in place" systems, such as are found in dairies and breweries. The method hereof involves the circulation of the sanitizing solution through the system at ambient temperatures followed by an optional rinse phase with potable water.

The type and amount of the above-listed components can be varied so that compositions having foaming properties from non-foaming to high-foaming can be produced.

For a more complete understanding of the present invention, reference is made to the following detailed description and accompanying examples.

DETAILED DESCRIPTION OF THE PREFERRED EMBODIMENT

The antimicrobial sanitizing composition of the present invention is predicated on the unexpected discovery that certain dicarboxylic acids exhibit enhanced antimicrobial activity, at pH levels at or below about 5.0.

The term "sanitizing" as used herein to indicate reduction of undesirable microorganisms by about five orders of magnitude or greater within time periods set forth below.

The antimicrobial sanitizing composition concentrate of the present invention, as noted, generally, comprises:

(a) a dicarboxylic acid having the general formula:

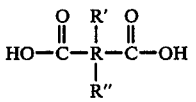

wherein R is a saturated or unsaturated hydrocarbon moiety having two carbon atoms; R' is selected from the group consisting of n-alkyl and n-alkenyl radicals having 6 to 12 carbon atoms; R' may be further substituted, suitable substituents are selected from the group consisting of thiols, methane thiols, amines, methoxy compounds, aryls and mixtures thereof, and R" may be hydrogen, or an alcohol;

(b) a solubilizer;
   (c) an anionic diluent; and
   (d) an acid present in an amount sufficient to yield a use solution pH at or below 5.0.

The concentrate, generally, comprises:

(a) from about 0.25 to about 25 percent, by weight, of the dicarboxylic acid, based on the total weight of the concentrate;

(b) from about 0.25 to about 20.0 percent, by weight, based on the total weight of the concentrate, of the solubilizer;

(c) from about 10.0 to about 95.5 percent, by weight, based on the total weight of the concentrate, of the diluent; and (d) from about 4.0 to about 50.0 percent, by weight, based on the total weight of the concentrate, of the acid.

The antimicrobial sanitizing composition of the present invention in its concentrated form can be effectively diluted with water or another suitable diluent such as various short-chain alcohols to provide a use solution having between about 10 ppm and about 500 ppm of the dicarboxylic acid while maintaining the pH at or below 5.0 without compromising the effectiveness of the solution.

The preferred dicarboxylic acids employed in the present invention are those having a four-carbon saturated or unsaturated backbone. Specifically, the substituted dicarboxylic acids employed herein are selected from the group consisting of succinic acid, maleic acid and fumaric acid and, preferably, succinic acid. The preferred succinic acids employed in the present invention are selected from the group consisting of n-octyl succinic acid, n-octenyl succinic acid, n-nonyl succinic acid, n-nonenyl succinic acid, n-decyl succinic acid, n-decenyl succinic acid, n-hexylsuccinic acid, n-hexenyl succinic acid, diisobutenyl succinic acid, methyl heptenyl succinic acid and mixtures thereof.

Without being bound to any theory, the unexpected efficacy of the dicarboxylic acid moiety over monocarboxylic equivalents appears to be related to the lower vapor pressures of the dicarboxylic acid moieties. The lower vapor pressures aid in keeping the resulting sanitizer use solution free from undesirable organoleptic properties associated with organic acids. Furthermore, it appears that straight-chain unsaturation increases the solubility of the material in an aqueous environment without adversely affecting antimicrobial properties.

The solubilizer employed herein is a surfactant hydrotrope capable of solubilizing the dicarboxylic acid in an acidic diluent while maintaining the dicarboxylic in solubilized form in both the concentrate and the diluted use solution of the product under use conditions. Various anionic, zwitterionic and nonionic surfactants or mixtures thereof can be successfully employed in the present invention.

Among the anionic surfactants useful herein are the alkyl sulfonates and alkyl aryl sulfonates having from about 8 to about 22 carbon atoms in the alkyl portion, as well as the alkali metal salts thereof. Commercially important are the linear alkyl sulfonate sodium and potassium salts such as sodium lauryl sulfonate, sodium xylene sulfonate and the sodium and potassium alkyl benzene sulfonates such as are described in U.S. Pat. Nos. 2,220,009 and 2,477,383.

The zwitterionic surfactants contemplated herein are the alkyl imidazolines and alkylamines marketed under the brand name MIRAPON by Miranol.

Among the nonionic surfactants useful in the composition of this invention are the ethylene oxide adducts of primary $C_8$ to $C_{12}$ alcohols sold commericially under the names NEODOL by Shell and ethylene oxide/propylene oxide adducts of ethylene glycol sold commercially under the names PLURAFAC and PLURONIC by BASF Corporation. Also useful are various alkylene glycols; specifically those containing 2 to 6 carbon atoms.

The anionic diluent employed is, preferably, potable drinking water. However, other compatible diluents such as $C-$ to $C-$ short-chain alcohols, may be employed.

As noted hereinabove, the antimicrobial sanitizing concentrate of the present invention also contains an acid capable of providing a solution pH at or below about 5.0 when the concentrate is diluted to its use solution strength. The acid employed must be compatible with the other components of the antimicrobial sanitizing solution, i.e., it must not produce instability or cause undue degradation of the surfactant or dicarboxylic acid. The acid can be either a weak organic acid such as acetic acid, hydroxyacetic acid, citric acid, tartaric acid, maleic acid, fumaric acid or mixtures thereof or an inorganic acid such as phosphoric acid, sulfuric acid, sulfamic acid or mixtures thereof. Preferably, phosphoric acid is employed.

The concentrate hereof is, generally, prepared by mixing the components together at ambient conditions, with heating, if necessary.

The concentrate hereof, as noted, is capable of forming a use solution when the concentrate is admixed with an anionic diluent such as water. The use solution thus formed generally comprises:

(a) from about 10 parts per million (ppm) to about 500 ppm of the dicarboxylic acid;

(b) from about 10 ppm to about 500 ppm of the surfactant hydrotrope-solubilizer;

(c) any diluent originally present in the concentrate;

(d) quantities of the organic or inorganic acid noted above sufficient to yield a use solution pH below about 5.0; and (e) an anionic diluent as the balance of the composition.

The antimicrobial sanitizing composition of the present invention may be successfully employed in sanitizing and disinfecting fixed-in-place food processing facilities such as those found in dairies, breweries and beverage plants. The composition of the present invention exhibits antimicrobial activity at ambient temperature.

To sanitize, the diluted use solution is circulated through the system for an interval sufficient to contact and kill undesirable microorganisms. This can be anywhere from less than about 30 seconds to about 10 minutes depending on the type and amount of contamination present. Ordinarily, the contact-time will be in the range of about one minute to about two minutes. After sanitizing, the sanitizing composition is drained from the system.

In most cleaned-in-place applications, the system can be brought back into service immediately after the sanitizing solution is removed. However, the system may be rinsed with potable water or any other suitable material after sanitizing.

For a more complete understanding of the present invention, reference is made to the following examples. The examples are to be construed as illustrative and not limitative of the present invention.

EXAMPLE I

Decyl succinic acid was prepared from decyl succinic anhydride by thermal hydrolysis. Two solutions of decyl succinic acid were prepared. A quantity of 75 percent phosphoric acid was added to one of the decyl succinic acid solutions such that the resulting solution contained 1 percent decyl succinic acid and 15 percent phosphoric acid. The remaining decyl succinic acid solution contained 1 percent succinic acid with no additives.

A one-part sample of the acidified decyl succinic acid solution was admixed with 100 parts of water having 500 ppm synthetic water hardness present as calcium carbonate to yield a solution containing 100 ppm decyl succinic acid. The resulting senitizing solution was exposed to challenge bacteria *Staphylococcus aureaus* ATCC 6538 and *Escherichia coli* ATCC 11229 to determine antimicrobial effectiveness. The test procedure employed was the Germicidal and Detergent Sanitizer Test recommended by the Association of Official Analytical Chemists. The test was carried out at 77° F. and the results are found in Table I.

A 50 ppm sample and a 25 ppm sample of the diluted acidified decyl succinic acid solution were prepared by admixing 0.5 part and 0.25 part samples of acidified 1 percent decyl succinic acid solutions, respectively, with 100 parts water containing 500 ppm hardness present as calcium carbonate ($CaCO_3$). The samples were exposed to the challenge bacteria *E. coli* and *Staph. aureus*, according to the A.O.A.C. test procedures outlined above. The results are found in Table I.

A sample containing 100 ppm of the non-acidified decyl succinic acid sample was also prepared using water having 500 ppm hardness and was exposed to the challenge bacteria. The resulting data is also found in Table I.

As can be seen from the data in Table I, the decyl succinic acid solution exhibited bacteriocidal activity under acidic conditions.

TABLE I

Evaluation of Antimicrobial Activity of Decyl Succinic Acid

| Formulation (% by weights) | Dilution (mls of Formulation per 100 ml water) | Amount of Succinic Acid Derivative (ppm) | Staph. aureus 30 sec. | Staph. aureus 60 sec. | E. coli 30 sec. | E. coli 60 sec. |
|---|---|---|---|---|---|---|
| a. 1 percent decyl succinic acid in water | 1.0 | 100 | <99.99 | <99.99 | <99.99 | <99.99 |
| b. 1 percent decyl succinic acid with 15 percent phosphoric acid in water | 1.0 | 100 | ≧99.999 | ≧99.999 | ≧99.999 | ≧99.999 |
| | 0.5 | 50 | ≧99.999 | ≧99.999 | ≧99.999 | ≧99.999 |
| | 0.25 | 25 | ≧99.999 | ≧99.999 | ≧99.999 | ≧99.999 |

EXAMPLE II

The antimicrobial acitivity of n-octyl, n-octenyl and n-decenyl succinic acids were evaluted according to the procedure discussed in Example I using *Staph. aureus* as the challenge bacteria. The resulting data are found in Table II.

As can be seen from the date in Table II, n-octyl, n-octenyl and n-decenyl succinic acids exhibit microbiocidal activity in the presence of acidic solutions in concentrations at or above 100 ppm dicarboxylic acid even in water having a hardness of 500 ppm present as calcium carbonate.

TABLE II

Evaluation of Antimicrobial Activity of Decyl Succinic Acid

| Formulation (% by weights) | Dilution (mls of Formulation per 100 ml water) | Amount of Succinic Acid Derivative (ppm) | Percent kill, Staph. aureus 30 sec. | Staph. Aureus 60 sec. |
|---|---|---|---|---|
| a. 5.0 percent n-octenyl n-succinic acid 10.0 percent sodium xylene sulfonate, 40.0 percent phosphoric acid and 45 percent water | 0.4 | 200 | ≧99.999 | ≧99.999 |
| | 0.25 | 100 | ≧99.999 | ≧99.999 |
| | 0.1 | 50 | ≧99.99 | ≧99.99 |
| b. 5.0 percent n-octyl succinic acid, 10.0 percent sodium xylene sulfonate, 40.0 percent phosphoric acid and 45 percent water | 0.4 | 200 | ≧99.999 | ≧99.999 |
| | 0.25 | 100 | ≧99.999 | ≧99.999 |
| | 0.1 | 50 | ≧99.99 | ≧99.99 |
| c. 5.0 percent n-decyl succinic acid, 8.0 percent sodium xylene sulfonate, 50.0 percent phosphoric acid and 37 percent water | 0.4 | 300 | ≧99.999 | ≧99.999 |
| | 0.2 | 100 | ≧99.999 | ≧99.99 | a. water containing 500 ppm synthetic hardness (as Calcium Carbonate)

EXAMPLE III

An antimicrobial sanitizing composition containing n-octenyl succinic acid, sodium xylene sulfonate (a surfactant hydrotrope), phosphoric acid and water was tested according to the guidelines discussed in Example I. The challenge yeast *Candida albicans* ATCC 14053 was employed. The *C. albians* used was grown on Saboraud's agar for 24 hours at 30° F. on a rotary shaker to ensure a sufficient number of challenge organisms. The resulting data are found in Table III.

As is shown by the data found in Table III, an antimicrobial acid sanitizing solution containing a succinic acid derivatives exhibits yeasticidal activity.

phoric acid and equal parts sodium xylene sulfonate and of one of the dicarboxylic acids listed in Table V. The balance of each use solution was water.

The challenge yeast *Saccharomyces cerevisiae* ATCC 7754 was grown on Saboraud's agar for 48 hours at 30° C. Cell suspensions made from this growth were tested

TABLE III

Evaluation of Yeasticidal Activity of n-Octenyl Succinic Acid

| Formulation, by weight | Mls of Formulation per 100 ml water[a] | Amount of Succinic Acid Derivative (ppm) | Percent kill of *C. albians* Detected at Given Intervals | | |
|---|---|---|---|---|---|
| | | | 5 min. | 10 min. | 15 min. |
| 5 percent n-octenyl succinic acid; 40 percent phosphoric acid; and | 0.4 | 200 | <99.99 | <99.99 | <99.99 |
| 10 percent xylene sulfonate 45 percent water | 0.8 | 400 | ≧99.999 | ≧99.999 | ≧99.999 |

[a]Water containing 500 ppm synthetic hardness as calcium carbonate.

EXAMPLE IV

Antimicrobial sanitizing use solutions were prepared. Each solution contained 500 ppm sodium xylene sulfonate, 0.15 percent phosphoric acid and 500 ppm of one of the dicarboxylic acids listed in Table IV. The balance of each use solution was water.

Each solution was tested against challenge bacteria *E. coli* and *Staph. aureus* according to the procedure outlined in Example I to determine bacteriocidal activity. The results are found in Table IV.

As is shown by the data found in Table IV, dicarboxylic acid derivatives of various n-alky n-alkenyl or branched carbon chain groups show bacteriocidal activities under acidic conditions.

TABLE IV

Evaluation of Bacteriocidal Activity of Various n-Alkyl, n-Alkenyl or Branched Succinic Acids Under Acidic Conditions

| | | Percent Kill | | | |
|---|---|---|---|---|---|
| | | Staph. aureus | | E. coli | |
| Compound | PPM | 30 Sec | 60 Sec | 30 Sec | 60 Sec |
| n-Hexyl Succinic Acid | 500 | ≧99.999 | ≧99.999 | ≧99.999 | ≧99.999 |
| n-Decyl Succinic Acid | 500 | ≧99.999 | ≧99.999 | <99.99 | <99.99 |
| n-Dodecyl Succinic Acid | 500 | ≧99.999 | ≧99.999 | <99.99 | <99.99 |
| n-Hexenyl Succinic Acid | 500 | <99.99 | ≧99.999 | <99.99 | <99.99 |
| n-Dodecenyl Succinic Acid | 500 | ≧99.999 | ≧99.999 | <99.99 | <99.99 |
| Diisobutenyl Succinic Acid | 300 | ≧99.999 | ≧99.999 | ≧99.999 | ≧99.999 |
| Methyl Heptenyl Succinic Acid | 300 | >99.999 | ≧99.999 | ≧99.999 | ≧99.999 |
| Nonenyl Succinic Acid | 300 | ≧99.999 | ≧99.999 | ≧99.999 | ≧99.999 |

Each test solution contained an amount of sodium xylene sulfonate equal to that of the dicarboxylic acid derivative and 0.15 percent, by weight, phosphoric acid.

EXAMPLE V

Various antimicrobial sanitizing use solutions were prepared. Each solution contained 0.15 percent phosphoric acid and equal parts sodium xylene sulfonate and of one of the dicarboxylic acids listed in Table V. The balance of each use solution was water.

The challenge yeast *Saccharomyces cerevisiae* ATCC 7754 was grown on Saboraud's agar for 48 hours at 30° C. Cell suspensions made from this growth were tested against the use solutions listed in Table V according to the guidelines discussed in Example I. The results are found in Table V.

As is shown by the data found in Table V, the dicarboxylic acid derivatives of various n-alkyl and n-alkenyl grops show yeasticidal activities under acidic conditions.

TABLE V

Evaluation of Yeasticidal Activity of Various Succinic Acids Under Acidic Conditions

| | | Percent Kill *Saccharomyces cerevisiae* Detected at given intervals | |
|---|---|---|---|
| Compound | PPM | 5 Min | 10 Min |
| n-Octenyl Succinic Acid | 600 | ≧99.999 | ≧99.999 |
| | 800 | ≧99.999 | ≧99.999 |
| n-Decenyl Succinic Acid | 300 | ≧99.999 | ≧99.999 |
| | 600 | ≧99.999 | ≧99.999 |
| n-Octyl Succinic Acid | 300 | <99.99 | ≧99.99 |
| | 600 | ≧99.999 | ≧99.999 |
| Methyl Heptenyl Succinic Acid | 600 | <99.99 | ≧99.999 |
| | 800 | ≧99.999 | ≧99.999 |

Each test solution contained an amount of sodium xylene sulfonate equal to that of the dicarboxylic acid derivative and 0.15 percent, by weight, of phosphoric acid.

EXAMPLE VI

Five different antimicrobial sanitizer use solutions compositions each containing 500 ppm n-octenyl succinic acid, 500 ppm sodium xylene sulfate and sufficient amounts of disodium hydrogen phosphate and citric acid to give the five sanitizer compositions a pH of 3.0, 3.4, 3.9, 4.4 and 4.9, respectively. Each composition was tested according to the procedure discussed in Example I using *Staph. aureus* and *E. coli* as the challenge bacteria.

As shown by the data in Table VI, antimicrobial compositions containing n-octenyl succinic acid are efficacious in killing challenge bacteria at pH levels below about 5.0.

TABLE VI

Evaluation of Bacteriocidal Activity of n-Octenyl Succinic Acid at Various pH Levels

| Compound, ppm | | Citrate | Percent Kill | | | |
|---|---|---|---|---|---|---|
| | | | Staph. aureus | | E. coli | |
| n-Octenyl Succinic Acid | Sodium Xylene Sulfonate | Phosphate Buffer, pH | 30 Sec | 60 Sec | 30 Sec | 60 Sec |
| 500 | 500 | 3.0 | ≧99.999 | ≧99.999 | ≧99.999 | ≧99.999 |
| 500 | 500 | 3.4 | ≧99.999 | ≧99.999 | ≧99.999 | ≧99.999 |
| 500 | 500 | 3.9 | ≧99.999 | ≧99.999 | ≧99.999 | ≧99.999 |
| 500 | 500 | 4.4 | ≧99.999 | ≧99.999 | ≧99.99 | ≧99.999 |
| 500 | 500 | 4.9 | <99.99 | <99.99 | <99.99 | <99.99 |

EXAMPLE VII

A concentrated antimicrobial solution was prepared according to the present invention. N-Octenyl succinic acid was prepared by the thermal hydrolysis of 1394 grams of n-octenyl succinic anhydride with 200 grams of water. Seven hundred and ninety-five grams of n-octenyl succinic acid was admixed with 757 grams of sodium xylene sulfonate and 3652 grams of tap water. The resulting solution was then acidified with 4258 grams of 75 percent phosphoric acid. The resulting composition is designated Composition A and is set forth in Table VII.

In order to make a use solution from the sanitizing concentrate which contains 200 ppm of n-octenyl succinic acid, 0.195 ml of the formulation Composition A (specific gravity 1.24) was admixed with 100 ml of water having a synthetic hardness of 500 ppm expressed as calcium carbonate. The resulting solution had a pH of 2.54.

A second composition was made in which the n-octenyl succinic acid was omitted. This composition is designated Composition B and is also set forth in Table VII.

A third composition was made in which an equal amount of n-decenyl succinic acid was substituted for the n-octenyl succinic acid. The resulting composition is set forth in Table VII as Composition C.

A fourth composition was prepared containing linear alkyl benzene sulfonate, phosphoric acid and water. The resulting composition is designated as Composite D and is set forth in Table VII.

The compositions A, B and C were diluted with water containing 500 ppm synthetic hardness in the amounts shown in Tables VIII and IX. These samples were tested according to the method disclosed in Example I using the challenge bacteria Staph. aureus and E. coli. The results are presented in Table VIII. The diluted samples in compositions A, B and C were tested according to procedure outlined in Example VI using the challenge yeasts Candida albicans and Saccharomyces cerevisiae. The results are found in Table IX.

Diluted sanitizer concentrates containing dicarboxylic acids and prepared according to the present invention are more effective against Staph. aureus and E. coli than those solutions in which the dicarboxylic acid is omitted as is indicated by the data in Table VIII.

As shown from the data in Table IX diluted sanitizer concentrates containing dicarboxylic acids exhibit yeasticidal activity far greater than those that do not contain dicarboxylic acids.

TABLE VI

| Compound | Amount (% by Weight) |
|---|---|
| COMPOSITION A: | |
| n-Octenyl Succinic Acid | 8.0 |
| Sodium Xylene Sulfonate | 8.0 |
| 75% Phosphoric Acid | 45.0 |
| Tap Water | 39.0 |
| COMPOSITION B: | |
| Sodium Xylene Sulfonate | 8.0 |
| 75% Phosphoric Acid | 45.0 |
| Tap Water | 47.0 |
| COMPOSITION C: | |
| n-Decenyl Succinic Acid | 8.0 |
| Sodium Xylene Sulfonate | 8.0 |
| 75% Phosphoric Acid | 45.0 |
| Tap Water | 39.0 |
| COMPOSITION D: | |
| Linear Alkyl Benzene Sulfonate | 2.5 |
| 75% Phosphoric Acid | 20.0 |
| Tap Water | 77.5 |

TABLE VIII

Comparison of Bacteriocidal Activity of Compositions A, B and C

| | Use Concentration mls/100 ml | Percent Kill | | | |
|---|---|---|---|---|---|
| | | Staph. aureus | | E. coli | |
| | | 30 Sec | 60 Sec | 30 Sec | 60 Sec |
| Composition A (from Table VII) | 0.2 | >99.999 | >99.999 | >99.999 | >99.999 |
| Composition B (from Table VII) | 0.8 | <99.99 | <99.99 | <99.99 | <99.99 |
| Composition C (from Table VII) | 0.2 0.3 0.4 | | | | |

TABLE IX

Comparison of Yeasticidal Activity of Compositions A, B and C

| | Use Concentration mls/100 ml | Percent Kill Candida albicans | | | |
|---|---|---|---|---|---|
| | | 5 min | 10 min | 15 min | 20 min |
| Composition A (from Table VI) | 0.4 | <99.99 | <99.99 | <99.99 | <99.99 |
| | 0.6 | ≧99.999 | ≧99.999 | ≧99.999 | ≧99.999 |

TABLE IX-continued

Comparison of Yeasticidal Activity of Compositions A, B and C

| | Use Concentration mls/100 ml | Percent Kill Candida albicans | | | |
|---|---|---|---|---|---|
| | | 5 min | 10 min | 15 min | 20 min |
| Composition B (from Table VII) | 0.8 | <99.99 | <99.99 | <99.99 | <99.99 |
| Composition C (from Table VII) | 0.1 | ≧99.999 | ≧99.999 | ≧99.999 | ≧99.999 |
| | 0.2 | ≧99.999 | ≧99.999 | ≧99.999 | ≧99.999 |

EXAMPLE VIII

The foaming properties of compositions prepared according to the present invention were evaluated. Compositions A, C and D listed in Table VII were compared. Use solutions of Compositions A, C and D were prepared by diluting a portion of the respective composition with water containing 500 ppm synthetic hardness present as calcium carbonate. The dilution standards are set forth in Table X.

Five hundred milliliter samples of each of the diluted Compositions A, C and D were each placed in a transparent cylinder. Each solution was circulated at a rate of 2 liters per minute for three minutes at 25° C. and was allowed to fall back into the cylinder on a baffle to generate foam. After three minutes, the circulation was stopped and the foam height recorded. The results are presented in Table X.

It was found that Composition A showed minimal foaming activity even when tested at a concentration four times above the conventional use levels of 200 ppm. However, Composition C which contained a different dicarboxylic acid showed high levels of foam comparable to Composition D, a known high-foaming composition. Thus, the microbial sanitizing compositions of the present invention can be either high-foaming or low-foaming depending on the choice of dicarboxylic acid.

TABLE X

Foaming Ability of Compositions A, B and C

| | Dilution (%) v/v | Dicarboxylic Acid (ppm) | Foam Height (cm) After Given Intervals | |
|---|---|---|---|---|
| | | | 15 sec | 30 sec |
| Composition A (from Table VII) | .195 | 200 | 0.0 | 0.0 |
| | .585 | 600 | 0.0 | 0.0 |
| | .78 | 800 | 1.5 | 1.0 |
| Composition C (from Table VII) | .195 | 200 | 46.0 | 28.0 |
| Composition D (from Table VII) | .78 | a | 41.0 | 38.0 |

$^a$contains 200 ppm linear alkyl benzene sulfonate rather than dicarboxylic acid.

EXAMPLE IX

Minimum inhibitory concentrations (mic) of n-alkenyl succinic acid derivatives effective against gram positive microorganisms were determined using differing concentrations of n-octenyl succinic acid and n-decenyl succinic acid in 10 ml of nutrient broth for tests against Staph. aureus and Saboraud's broth for tests against Saccharomyces cerevisiae. These concentrations of succinic acid derivatives were inoculated with 0.1 ml of a 1 to 100 dilution of the challenge cultures. The challenged concentrations were incubated for 24 hours at 37° C. in the case of Staph. aureus and 30° C. in the case of Saccharomyces cerevisiae. Presence or absence of growth was recorded.

The results collected in Table XI indicate that n-octenyl succinic acid has a minimum inhibitory concentration of 1000 ppm against Staph. aureus. N-decenyl succinic acid showed a minimum inhibitory concentration of 1000 against Staph. aureus and 500 ppm against Saccharomyces cerevisiae.

TABLE XI

Inhibition of Gram Positive Microorganisms by Succinic Acid Derivatives at Various Concentrations

| | 50 ppm | 100 ppm | 250 ppm | 500 ppm | 1000 ppm |
|---|---|---|---|---|---|
| | n-Decenyl succinic acid | | | | |
| Staph. aureus | + | + | + | + | − |
| Saccharomyces cerevisiae | + | + | + | − | − |
| | n-Octenyl succinic acid | | | | |
| Staph. aureus | + | + | + | + | − |
| Saccharomyces cerevisiae | + | + | + | + | + |

+ indicates growth
− indicates no growth

It is to be appreciated from the preceding that there has been described herein a sanitizer concentrate and use solution which is efficacious in killing off both gram negative and gram positive bacteria as well as yeasts.

Having, thus, described the invention, what is claimed is:

1. An antimicrobial concentrate composition capable of being diluted with a major amount of water to form an antimicrobial solution, the concentrate composition comprising:

(a) a dicarboxylic acid having the general formula:

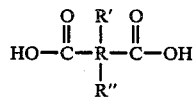

wherein R is a saturated or unsaturated hydrocarbon moiety having two carbons; R' is a substituted or unsubstituted n-alkyl or n-alkenyl moiety having between about 6 and about 12 carbon atoms; and R" is a substituent selected from the group consisting of hydrogen and alcohol, the dicarboxylic acid being present in an amount between about 0.25 and about 25 percent by weight based on the total weight of the concentrate;

(b) a solubilizer present in an amount between about 0.25 and about 20 percent by weight based on the total weight of the concentrate;

(c) an acid present in an amount capable of yielding a solution pH below about 5.0 upon dilution of the concentrate to a use solution; and (d) an anionic diluent, the diluent selected from the group consisting of alcohols, water and mixtures thereof, the diluent being present in an amount between about 10.0 and about 95 percent by weight based on the total weight of the concentrate.

2. The concentrate composition of claim 1 wherein R' is a linear hydrocarbon.

3. The concentrate composition of claim 1 wherein R' has between about 8 and about 10 carbon atoms.

4. The concentrate composition of claim 1 wherein R' is a substituted moiety, the substituent being selected from the group consisting of thio functional groups, methane thiol functional groups, amine functional groups, methoxy functional groups, aryl functional groups and mixtures thereof.

5. The concentrate composition of claim 1 wherein the dicarboxylic acid is selected from the group consisting of n-octyl succinic acid, n-octenyl succinic acid, n-nonyl succinic acid, n-nonenyl succinic acid, n-decyl succinic acid, n-decenyl succinic acid, n-hexyl succinic acid, n-hexenyl succinic acid, diisobutenyl succinic acid, methyl heptenyl succinic acid and mixtures thereof.

6. The concentrate composition of claim 1 wherein the R is selected from the group consisting of succinic acid, maleic acid and fumaric acid.

7. The concentrate composition of claim 1 wherein the acid is a weak organic acid selected from the group consisting of acetic acid, hydroxyacetic acid, citric acid, tartaric acid, maleic acid, fumaric acid or mixtures thereof.

8. The concentrate composition of claim 1 wherein the acid is an inorganic acid selected from the group consisting of phosphoric acid, sulfuric acid, sulfamic acid and mixtures thereof.

9. The concentrate composition of claim 1 wherein the acid is a mixture of an inorganic acid and an organic acid; the inorganic acid selected from the group consisting of phosphoric acid, sulfuric acid, sulfamic acid or mixtures thereof, the organic acid selected from the group consisting of acetic acid, hydroxyacetic acid, citric acid, tartaric acid, maleic acid, fumaric acid or mixtures thereof.

10. The concentrate composition of claim 1 wherein the solubilizer is a surfactant-hydrotrope selected from the group consisting of anionic surfactants, nonionic surfactants, zwitterionic surfactants or mixtures thereof.

11. The concentrate composition of claim 10 wherein the anionic surfactant is selected from the group consisting of alkyl sulfonates and alkyl aryl sulfonates having about 8 to about 22 carbon atoms in the alkyl portion, alkali metal salts or mixtures thereof.

12. The concentrate composition of claim 9 wherein the zwitterionic surfactant is selected from the group consisting of alkyl imidazolines, alkyl amines or mixtures thereof.

13. The concentrate composition of claim 10 wherein the nonionic surfactant is selected from the group consisting of ethylene oxide adducts of $C_8$ to $C_{12}$ alcohols, ethylene oxide/propylene oxide adducts of ethylene glycol, alkylene glycols or mixtures thereof.

14. The concentrate composition of claim 1 comprising:
(a) between about 0.25 and about 20.0 percent, by weight of the total composition, of the dicarboxylic acid;
(b) between about 0.25 and about 20.0 percent, by weight of the total composition, of the solubilizer;
(c) between about 10.0 and about 95.5 percent, by weight of the total composition, of the diluent; and
(d) between about 4.0 and about 50.0 percent, by weight of the total composition, of the acid.

15. An aqueous, antimicrobial composition consisting essentially of:
(a) between about 10 ppm and about 500 ppm of a dicarboxylic acid having the general formula:

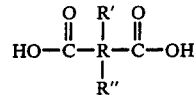

wherein R is a saturated or unsaturated hydrocarbon moiety having two carbon atoms; R' is a substituted or unsubstituted n-alkyl or n-alkenyl moiety having between about 6 and about 12 carbon atoms, and R" is a functional group selected from the group consisting of hydrogen and alcohols;
(b) between about 10 ppm and about 500 ppm of a solubilizer;
(c) sufficient acid to yield a pH below about 5.0; and
(d) water to make up the balance.

16. The aqueous composition of claim 15 wherein the dicarboxylic acid is selected from the group consisting of n-octyl succinic acid, n-octenyl succinic acid, n-nonyl succinic acid, n-nonenyl succinic acid, n-decyl succinic acid, n-decenyl succinic acid, n-hexyl succinic acid, n-hexenyl succinic acid, diisobutenyl succinic acid, methyl heptenyl succinic acid and mixtures thereof.

17. The aqueous composition of claim 15 wherein the R is selected from the group consisting essentially of succinic acid, maleic acid and fumaric acid.

18. The aqueous composition of claim 15 wherein the acid is a weak organic acid selected from the group consisting of acetic acid, hydroxyacetic acid, citric acid, tartaric acid, maleic acid, fumaric acid or mixtures thereof.

19. The aqueous composition of claim 15 wherein the acid is an inorganic acid selected from the group consisting of phosphoric acid, sulfuric acid, sulfamic acid and mixtures thereof.

20. The aqueous composition of claim 15 wherein the acid is a mixture of an inorganic acid and an organic acid; the inorganic acid selected from the group consisting of phosphoric acid, sulfuric acid, sulfamic acid or mixtures thereof, the organic acid selected from the group consisting of acetic acid, hydroxyacetic acid, citric acid, tartaric acid, maleic acid, fumaric acid or mixtures thereof.

21. The aqueous composition of claim 15 wherein the solubilizer is a surfactant-hydrotrope selected from the group consisting of anionic surfactants, nonionic surfactants, zwitterionic surfactants or mixtures thereof.

22. The aqueous composition of claim 21 wherein the anionic surfactant is selected from the group consisting of alkyl sulfonates and alkyl aryl sulfonates having about 8 to about 22 carbon atoms in the alkyl portion, the alkali metal salts thereof, and mixtures thereof.

23. The aqueous composition of claim 21 wherein the zwitterionic surfactant is selected from the group consisting of alkyl imidazolines, alkyl amines or mixtures thereof.

24. The aqueous composition of claim 21 wherein the nonionic surfactant is selected from the group consisting of ethylene oxide adducts of $C_8$ to $C_{12}$ alcohols, ethylene oxide/propylene oxide adducts of ethylene glycol, alkylene glycols or mixtures thereof.

25. The aqueous composition of claim 15 wherein the diluent is an anionic material selected from the group consisting of short-chain alcohols and water.

26. The aqueous composition of claim 15 wherein R' is a substituted moiety, the substituent being selected from the group consisting of thiol functional groups, methane thiol functional groups, amine functional groups, methoxy functional groups, aryl functional groups and mixtures thereof.

* * * * *

REEXAMINATION CERTIFICATE (1675th)
United States Patent [19]
Lopes et al.

[11] B1 4,715,980
[45] Certificate Issued Apr. 7, 1992

[54] ANTIMICROBIAL SANITIZING COMPOSITION CONTAINING N-ALKYL AND N-ALKENYL SUCCINIC ACID AND METHODS FOR USE

[75] Inventors: John A. Lopes; James H. Stanton, both of Grosse Ile, Mich.

[73] Assignee: Diversey Wyandotte Corporation

Reexamination Request:
No. 90/002,349, Feb. 20, 1991

Reexamination Certificate for:
Patent No.: 4,715,980
Issued: Dec. 29, 1987
Appl. No.: 840,336
Filed: Mar. 17, 1986

[51] Int. Cl.$^5$ .................. C11D 3/48; C11D 7/08
[52] U.S. Cl. .................. 252/106; 252/174.19; 252/174.21; 252/142; 252/542; 252/554; 252/558; 252/DIG. 14; 422/28; 514/557; 514/558
[58] Field of Search .................. 252/106

[56] References Cited

U.S. PATENT DOCUMENTS

| | | | |
|---|---|---|---|
| 3,560,507 | 2/1971 | Wakeman | 260/286 |
| 4,002,775 | 1/1977 | Kabara | 426/532 |
| 4,247,569 | 1/1981 | Hata et al. | 426/335 |
| 4,277,378 | 7/1981 | Tsujii et al. | 252/546 |
| 4,404,040 | 9/1983 | Wang | 134/22.14 |

FOREIGN PATENT DOCUMENTS

| | | |
|---|---|---|
| 3229097A1 | 9/1984 | Fed. Rep. of Germany. |
| 0135898A2 | 4/1985 | Fed. Rep. of Germany. |
| 1504847 | 3/1978 | United Kingdom. |
| 2103089 | 2/1983 | United Kingdom. |

OTHER PUBLICATIONS

Adair, Frank W. et al., "Lytic Effects of Di- or Tricarboxylic Acids Plus Sodium Dodecyl Sulfate Against *Pseudomonas aeruginosa*," *Antimicrob. Agents Chemother.*, 16 (3), 417–20, Sep. 1979.

G. Thorn, "Effects of Various Fungicides in Soil on Water and Amino Acid Transport in Tomato Plants," *Can. J. Bot.*, 48 (11), 2033–6, 1970.

T. Iizuka, "Antibacterial Activity of Myrmicacin and Related Compounds on Pathogenic Bacteria in Silkworm Larvae, *Streptococcus faecalis* AD-4," *J. Fac. Agr., Hokkaido Univ.*, 59 (2), 262–6, 1979.

*Primary Examiner*—Prince E. Willis, Jr.

[57] ABSTRACT

An antimicrobial sanitizing composition concentrate suitable for use in food preparation and handling equipment and capable of being diluted with a major amount of diluent and the resulting aqueous use solution. The concentrate containing:

(a) a dicarboxylic acid having the general formula:

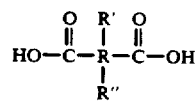

wherein R is a saturated or unsaturated hydrocarbon moiety having two carbon atoms; R' is a substituted or unsubstituted n-alkyl or n-alkenyl moiety having between about 6 and about 12 carbon atoms, and R" is a functional group selected from the group consisting of hydrogen, alcohols, amines and sulfates;

(b) a solubilizer;

(c) an acid capable of yielding a pH below about 5.0 upon dilution of the concentrate to a use solution; and (d) a diluent.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-26 is confirmed.

* * * * *